United States Patent [19]

Mulder

[11] Patent Number: 5,533,969
[45] Date of Patent: Jul. 9, 1996

[54] BALLOON CATHETER WITH PRESSURE INDICATOR

[75] Inventor: Martien Mulder, Roden, Netherlands

[73] Assignee: Cordis Corporation, Miami Lakes, Fla.

[21] Appl. No.: 276,525

[22] Filed: Jul. 18, 1994

[30] Foreign Application Priority Data

Jul. 29, 1993 [NL] Netherlands ............................ 9301329

[51] Int. Cl.⁶ ............................................. A61M 29/00
[52] U.S. Cl. ................................................ 604/100; 604/96
[58] Field of Search ............................... 604/96–100, 121, 604/118; 128/207.15

[56] References Cited

U.S. PATENT DOCUMENTS

| | | |
|---|---|---|
| 2,136,261 | 11/1938 | Anderson . |
| 4,088,135 | 5/1978 | O'Neill ................................. 604/100 |
| 4,159,722 | 7/1979 | Walker . |
| 4,185,638 | 1/1980 | Bruner . |
| 4,403,988 | 9/1983 | Binard et al. ........................... 604/118 |
| 4,552,558 | 11/1985 | Muto . |
| 4,623,335 | 11/1986 | Jackson ................................... 604/118 |
| 4,632,669 | 12/1986 | Phipps, Sr. et al. ..................... 604/118 |
| 5,336,183 | 8/1994 | Greelis et al. ........................... 607/97 |

FOREIGN PATENT DOCUMENTS

3839612C1  2/1990  Germany .

Primary Examiner—Corrine M. McDermott
Attorney, Agent, or Firm—Gerstman, Ellis & McMillin, Ltd.

[57] ABSTRACT

The invention relates to a balloon catheter comprising a tube with a distal and a proximal end and at least two lumens each of which is connected to a connecting piece by a single catheter section at the proximal end. A balloon is attached close to the distal end, an internal space of which is connected to one of the lumens through which it can be inflated with fluid. A pressure gauge is carried in the single catheter section connected to the one lumen leading to the balloon.

16 Claims, 1 Drawing Sheet

BALLOON CATHETER WITH PRESSURE INDICATOR

BACKGROUND AND SUMMARY OF THE INVENTION

This invention relates to a balloon catheter. Such a catheter comprises a tubular body having a distal end, a proximal end, and at least two lumens. At the proximal end each lumen is attached to a connector. A balloon has an interior connected to one of the lumens, and is attached to the catheter adjacent the distal end. Thus, a fluid under pressure can be supplied to and removed from the balloon in order to cause the balloon to swell to a greater or lesser degree.

Balloon catheters of this type are generally known, and are used for instance to dilate narrowed blood vessels. For this purpose the catheter is introduced in a patient, and the balloon is positioned in the area of the narrowing. By subsequently supplying fluid under pressure via the connector concerned, the balloon-shaped member will expand, thus pushing the narrowed portion outwards.

With such a treatment, it is essential that the fluid supplied to the balloon is of the right pressure. When there is not enough pressure, dilatation will be insufficient, whereas there will be a danger of trauma when the pressure is too great. The use of such a balloon catheter thus requires great skill on the part of the attending physician.

An object of the invention is to provide a balloon catheter of the type described which can be used to carry out the treatment with a greater chance of success. To this end, the balloon catheter according to the invention comprises a pressure gauge placed in a catheter section leading to the balloon. Such a pressure gauge can be made simple and tractable, hence not impeding the treatment. The pressure gauge will give the performing physician a clear indication of the pressure in the balloon, so that the treatment can be carried out effectively.

As an advantageous embodiment of the balloon catheter according to the invention, the pressure gauge forms part of the connection line to the balloon, providing a very manageable assembly.

In one advantageous embodiment, the pressure acts on opposed piston faces, creating a net reaction force in the direction of the smaller diameter of the opposed piston faces. The force increases proportionally with the pressure. A spring working against the movement of the prison is consequently pushed inwardly, proportional to the pressure, giving an indication of the prevailing pressure.

The piston can be seen directly through the transparent housing, so that this in itself can function directly as an indication member, together with a divided, numerical scale on the housing wall. A magnifying effect can occur at the rounded corners of the housing, allowing more accurate reading.

The invention will be explained in the following description with reference to the attached drawings.

DESCRIPTION OF SPECIFIC EMBODIMENTS

Figure 1:
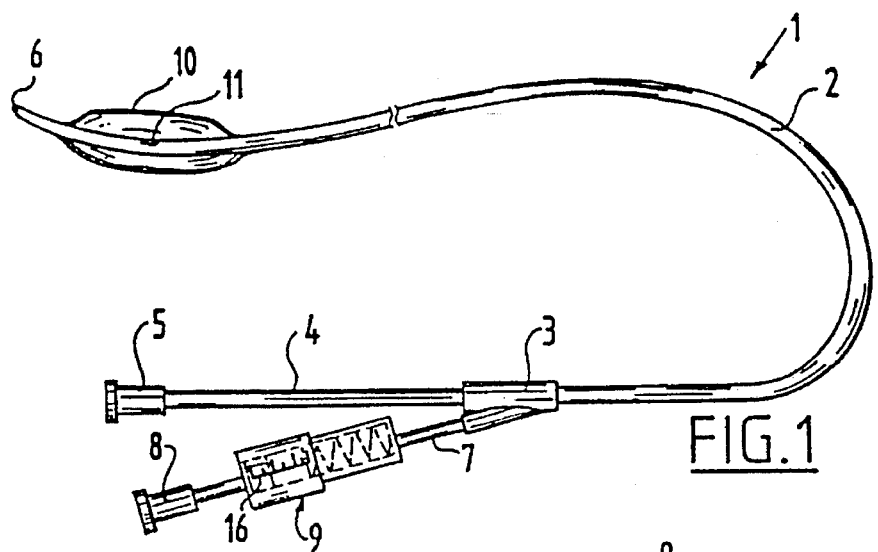
FIG. 1 represents a view of a balloon catheter according to the invention.

The balloon catheter 1 of FIG. 1 comprises a basic member 2 having, in this example, two lumens. Close to the proximal end, the basic member 2 is connected with a Y-piece 3 in which each of the two lumens is connected separately with one of the single catheter branch tubings 4, 7. The single catheter tubing 4 ends in a connector 5. The lumen linked to this is connected with an opening 6 at the distal end of the catheter 1, and serves for supplying contrast medium to the distal end of the catheter, for visibility on an X-ray screen during catheterization.

Via the above mentioned single catheter tubing 7, the second lumen is connected with a connector 8. The lumen connected to this tubing 7 ends in an opening 11 inside balloon 10 near the distal end of the catheter. By supplying fluid under pressure via the connector 8, catheter tubing section 7, and the lumen in the basic member 2 connected with it, pressure can be applied to the balloon 10, causing it to inflate.

According to the invention, a pressure gauge 9 is received in coaxial relation in the single catheter tubing section 7 which communicates with balloon 10. A numerical, pressure-indicating scale 16 is formed in housing 11, to provide an indication of the pressure in the line leading to the balloon 10 and hence of the pressure in the balloon 10 itself.

Figure 2:
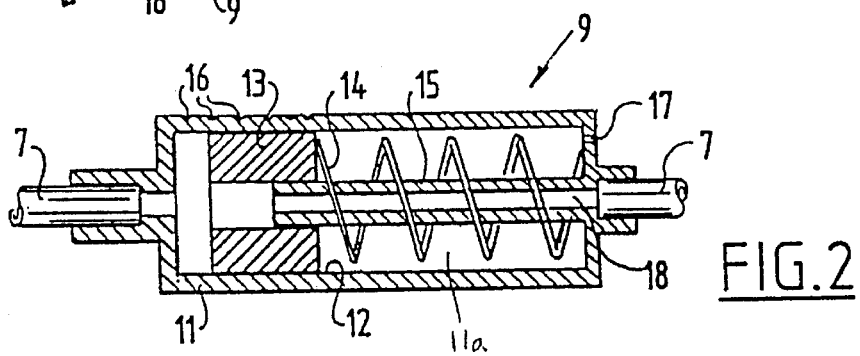
FIG. 2 shows a cross-section of a pressure gauge to be used with a catheter as shown in FIG. 1.

A cross-section of the pressure gauge 9 is shown in FIG. 2. In this embodiment, the pressure gauge comprises elongated housing 11 with an inlet and an outlet placed axially opposite each other, to which the parts of the catheter tubing 7 have been connected, for instance by means of gluing.

Inside the housing 11, a cylinder bore 12 is formed, in which a slide piston 13 is received. The piston 13 can also be moved along a guiding pin 15 which extends from the opposite end of the housing to inside the piston 13. Around its perimeter the piston forms a seal in the bore 12 and internally also around the guiding pin 15, so that a sealed chamber 11a is formed.

In chamber 11a, having a ring-shaped cross-section, a helical compression spring 14 is received to bias piston 13 in the left-hand direction as shown in FIG. 2.

The housing 11 is made of a transparent plastic material, on the outside of which indicating scale 16 is formed.

In the guiding pin 15, a continuous channel or lumen 18 is formed so that a continuous conduit is formed from the inlet to the outlet of the pressure gauge.

The pressure in the conduit acts on the left-hand surface of the piston 13 as seen in FIG. 2. With increasing pressure, the force consequently urging piston 13 in the right-hand direction will increase so that the piston 13 will be moved over a distance against the action of the spring 14 and increasing compression in chamber 11a until a state of equilibrium is reached. The position of the piston 13 thus relates to the scale 16 in a way that is a function of the pressure in the line. If desired, a bore hole 17 can be made in the housing for the escape of displaced air as the piston advances. This bore hole 17 is not absolutely necessary as the air in the area containing the spring is compressible, but when present it ensures that the displacement of the piston 13 occurs in a linear fashion with the pressure, dependent only on spring resistance. Alternatively, if chamber 11a is sealed, spring 14 can be eliminated since spring action is provided by air in the sealed chamber 11a.

Figure 3:
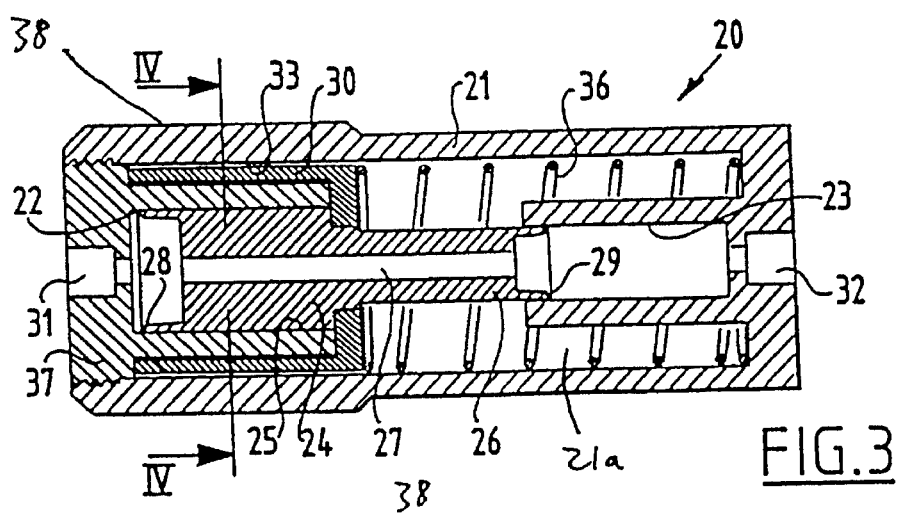
FIG. 3 shows another embodiment of a pressure gauge, also in cross-section.
Figure 4:
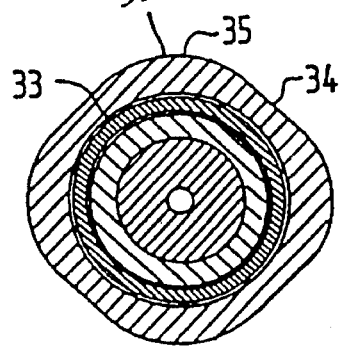
FIG. 4 represents a cross-section of the housing of the pressure gauge of FIG. 3 at section line IV—IV in FIG. 3.

The pressure gauge 20 as shown in FIG. 3 also comprises an elongated housing 21 with an inlet 31 and an outlet 32 on the opposite side, for connection with tubing of a catheter.

It does not matter as regards the proper functioning of the pressure gauges described here, in which position the inlet 31 and outlet 32 are received in the pressure line, i.e. which one comes first.

The housing 21 comprises a continuous borehole 33. At the left-hand side in FIG. 3, an insert 37 is received in the housing. In this insert 37 a first axial cylinder bore 22 is formed, being positioned opposite to a second axial cylinder bore 23 formed in housing 21. Second bore 23 has a smaller diameter than the first bore 22.

Piston 24 is provided with sections having different diameters. The left section 25 in FIG. 3 fits closely in the first cylinder bore 22, while the right piston section 26 fits closely in the second cylinder bore 23. A bore 27 extends through the center of piston 24, so that a continuous, sealed conduit is created from inlet 31, via bore 27, to outlet 32.

As FIG. 3 shows, a thin, annular, protruding edge 28 is formed at the end of wide section 25 of the piston. A similar thin, annular edge 29 is provided at the narrow end 26 of piston 24. These edges 28, 29 push outwards in a resilient manner, so that there is a good sealing contact of piston 24 with the bores 25 and 23 respectively.

A sleeve 30 is carried by piston 24, which sleeve extends in a tubular space with a ring-shaped cross-section between an insert 37 and the bore 33 of the housing 21. This sleeve 30 is of a contrasting color, to form a movable indicating member. Indicating member sleeve 30 acts together with scale 16 on the outside of the housing 21 to indicate the pressure sensed, as a function of the position of piston 22. Helical compression spring 36 in sealed chamber 21a urges piston 24 to the left at ambient pressure conditions.

The pressure in the bore between inlet 31 and outlet 32 acts on both ends of the piston 24 adjacent edges 28, 29. Consequently a force, proportional to the magnitude of the pressure, will be imposed to the right under elevated pressures in bore 27, because the piston end area surrounded by edge 28 is greater than the end area surrounded by edge 29. Subject to the pressure, the piston will move to the right against the force of the spring 36, and the pressure in sealed chamber 21a, until the force due to the piston pressure is in equilibrium with the opposing forces exerted by the spring 36 and the pressure of chamber 21a. The position of the sleeve 30 is therefore a function of the pressure. In other words, when the pressure increases, piston 24 and sleeve 30 will take up a position more to the right.

At the outer circumference of the housing 21, which is made of a transparent plastic material, a printed or embossed scale 38 is present, similar to that shown in the previous figures. An edge, and specifically here the left edge, of the sleeve 30 is made of a contrasting color, to indicate together with the scale specific pressures as read by the position of an end of sleeve 30 on the scale. In order to be able to see the end of the sleeve 30 properly, the circumference 34 of the housing has, where the scale division has been applied, the shape of a square with rounded corners 38.

The rounded corners have a smaller radius of curvature than the radius of the inner wall 33, so that at these corners a magnifying lens 35 is formed.

Instead of a scale on the outer surface of the housing, it is also possible to apply a scale to the outside of the insert 37, which will be covered to a greater or lesser degree by the sleeve 30. The magnifying effect at wall portion 35 ensures that the scale will appear to be larger.

The illustrated and described axial embodiment of the pressure gauges renders them exceptionally suitable for incorporation in a tubular catheter section, without them being an impediment. Other embodiments of the pressure gauge are also possible, however.

That which is claimed is:

1. A balloon catheter comprising an elongated catheter body having a distal end and a proximal end, said catheter body defining a lumen and a connector carried on the proximal end in communication with said lumen; a balloon attached adjacent to said distal catheter body end with said balloon being in communication with said lumen; a pressure gauge connected with said lumen in which said pressure gauge comprises an elongated housing carrying a spring and a numerical scale and having an inlet and an outlet spaced from each other; a piston in said housing movable against said spring by the pressure to be measured, in which said piston and scale work together to indicate a quantitative pressure reading.

2. The balloon catheter of claim 1 in which the housing defines an interior comprising a first axial cylinder bore and a second axial cylinder bore of smaller diameter, said cylinder bores being positioned respectively adjacent to opposed housing ends, said piston comprising parts which are sealingly slidable with each of said cylinder bores, said piston also defining a piston bore, wherein a continuous conduit is formed from the housing inlet through the first cylinder bore, through the piston bore, and through the second cylinder bore to the outlet.

3. The balloon catheter of claim 2 in which said housing comprises a transparent plastic material whereby the position of said piston relative to said scale can be seen.

4. The balloon catheter of claim 3 in which said spring occupies one of said cylinder bores.

5. The balloon catheter of claim 1 in which, at least in the vicinity of said scale, the housing defines a cross section of polygonal shape with rounded corners.

6. The balloon catheter of claim 1 in which said spring comprises a coil spring positioned in a vented chamber.

7. The balloon catheter of claim 1 in which said housing comprises a transparent plastic material whereby the position of said piston relative to said scale can be seen.

8. A balloon catheter comprising a tubular catheter body with a distal end and a proximal end, said catheter body having at least two lumens and separate connectors, each of said lumens communicating with a separate connector at the proximal end; a balloon attached close to the distal catheter body end, said balloon being in communication with one of said lumens; a pressure gauge connected in coaxial relation with said one lumen, wherein the pressure gauge comprises an elongated housing carrying a spring and numerical scale and having an inlet and an outlet placed axially opposite each other, and a piston in said housing, movable against said spring by the pressure to be measured, and wherein the piston and scale work together to indicate a quantitative pressure reading.

9. The balloon catheter of claim 8, wherein the inside of the housing comprises a first axial cylinder bore and a second axial cylinder bore with a smaller diameter, said cylinder bores being respectively adjacent opposed housing ends, the piston comprising two parts sealingly slidable with the cylinder bores respectively, and defining a piston bore, wherein a continuous conduit is formed from the housing inlet, through the first cylinder bore, through the piston bore, and through the second cylinder bore to the inlet.

10. The balloon catheter of claim 8 wherein the housing has been manufactured of a transparent plastic material, whereby the position of said piston relative to said scale can be seen.

11. The balloon catheter of claim 10 wherein at the scale the housing has a cross-section of polygonal shape with rounded corners.

12. The balloon catheter of claim 8 in which said spring occupies a sealed, air-filled chamber.

13. A balloon catheter comprising a tubular catheter body with a distal end and a proximal end, said catheter body having at least two lumens and separate connectors, each of said lumens communicating with a separate connector at the proximal end; a balloon attached close to the distal catheter body end, said balloon being in communication with one of said lumens; a pressure gauge connected in coaxial relation with a tube section that is in communication with said one lumen, wherein the pressure gauge comprises an elongated housing having a transparent portion, a spring, and carrying a numerical scale in said transparent portion of said housing, said housing having an inlet and an outlet positioned axially opposite each other, and a piston positioned in said housing, movable against said spring by the pressure to be measured, wherein the piston and scale work together to indicate a quantitative pressure reading; the inside of said housing comprising a first axial cylinder bore and a second axial cylinder bore with a smaller diameter, said cylinder bores being respectively positioned adjacent opposed housing ends, the piston comprising two parts sealingly slidable with the cylinder bores respectively, said piston also defining a piston bore, wherein a continuous conduit is formed from the housing inlet through the first cylinder bore, through the piston bore, and through the second cylinder bore to the outlet.

14. The balloon catheter of claim 13 in which at the scale the housing has a cross-section of a polygonal shape with rounded corners.

15. The balloon catheter of claim 14 in which said spring occupies a sealed, air-filled chamber.

16. The balloon catheter of claim 14 in which said spring comprises a coil spring positioned in a vented chamber.

* * * * *